United States Patent
Wang et al.

(10) Patent No.: US 10,429,093 B2
(45) Date of Patent: Oct. 1, 2019

(54) AIR TREATMENT SYSTEM

(71) Applicant: QINGDAO HAIER AIR CONDITIONER GENERAL CORP., LTD., Shandong (CN)

(72) Inventors: Youning Wang, Shandong (CN); Hongjin Wu, Shandong (CN); Zhenxue Zhu, Shandong (CN); Mingjing Fan, Shandong (CN); Jialan Zhuang, Shandong (CN); Yuanwei Dong, Shandong (CN)

(73) Assignee: QINGDAO HAIER AIR CONDITIONER GENERAL CORP., LTD., Shandong (CN)

( * ) Notice: Subject to any disclaimer, the term of this patent is extended or adjusted under 35 U.S.C. 154(b) by 315 days.

(21) Appl. No.: 15/323,076

(22) PCT Filed: Dec. 8, 2014

(86) PCT No.: PCT/CN2014/093283
§ 371 (c)(1),
(2) Date: Dec. 29, 2016

(87) PCT Pub. No.: WO2016/000411
PCT Pub. Date: Jan. 7, 2016

(65) Prior Publication Data
US 2017/0153040 A1    Jun. 1, 2017

(30) Foreign Application Priority Data

Jul. 3, 2014    (CN) .......................... 2014 1 0315032

(51) Int. Cl.
*B01D 53/02*    (2006.01)
*F24F 13/20*    (2006.01)
(Continued)

(52) U.S. Cl.
CPC ................ *F24F 13/20* (2013.01); *A61L 9/16* (2013.01); *A61L 9/20* (2013.01); *A61L 9/22* (2013.01);
(Continued)

(58) Field of Classification Search
CPC .......... A61L 2209/14; A61L 9/16; A61L 9/20; A61L 9/22; F16B 1/00; F16B 2001/0035;
(Continued)

(56) References Cited

U.S. PATENT DOCUMENTS 3,210,916 A * 10/1965 Jepson ...................... A47L 5/32
15/327.1
3,487,624 A * 1/1970 Tignanelli .............. B01D 46/10
34/82

(Continued)

FOREIGN PATENT DOCUMENTS

| CN | 2553292 Y | 5/2003 |
| CN | 2556548 Y | 6/2003 |

(Continued)

OTHER PUBLICATIONS

International Search Report and Written Opinion for Application No. PCT/CN2014/093283 dated Apr. 8, 2015.

(Continued)

*Primary Examiner* — Christopher P Jones
(74) *Attorney, Agent, or Firm* — Alston & Bird LLP

(57) ABSTRACT

An air handling system comprising: a top cover (1), a base (5) and at least one air handling device provided between the top cover (1) and the base (5), wherein the top cover (1) and the adjacent air handling device, the base (5) and the adjacent air handling device, and the adjacent air handling devices are all connected to each other by means of magnetic attraction.

7 Claims, 14 Drawing Sheets

(51) Int. Cl.
  *F24F 3/12*   (2006.01)
  *A61L 9/16*   (2006.01)
  *A61L 9/20*   (2006.01)
  *A61L 9/22*   (2006.01)
  *F16B 1/00*   (2006.01)
  *F24F 6/04*   (2006.01)
  *F24F 13/22*  (2006.01)
  *F24F 13/28*  (2006.01)
  *F24F 13/30*  (2006.01)
  *F24F 6/00*   (2006.01)

(52) U.S. Cl.
  CPC .................. *F16B 1/00* (2013.01); *F24F 3/12* (2013.01); *F24F 6/04* (2013.01); *F24F 13/222* (2013.01); *F24F 13/28* (2013.01); *F24F 13/30* (2013.01); *A61L 2209/14* (2013.01); *F16B 2001/0035* (2013.01); *F24F 2006/008* (2013.01); *F24F 2006/046* (2013.01); *F24F 2221/36* (2013.01)

(58) Field of Classification Search
  CPC .......... F24F 13/20; F24F 13/222; F24F 13/28; F24F 13/30; F24F 2006/008; F24F 2006/046; F24F 2221/36; F24F 6/04
  See application file for complete search history.

(56) References Cited

U.S. PATENT DOCUMENTS

| | | | | |
|---|---|---|---|---|
| 9,821,260 | B2* | 11/2017 | Stoner, Jr. | B01D 46/0023 |
| 2002/0171158 | A1* | 11/2002 | Bloemer | F24F 6/04 |
| | | | | 261/97 |
| 2002/0178704 | A1* | 12/2002 | Hilliard | B01D 46/0002 |
| | | | | 55/385.1 |
| 2005/0138905 | A1* | 6/2005 | Kubokawa | B01D 46/0016 |
| | | | | 55/497 |
| 2009/0199526 | A1* | 8/2009 | Wallace | B01D 46/0004 |
| | | | | 55/493 |
| 2010/0192768 | A1* | 8/2010 | Kim | B01D 45/14 |
| | | | | 95/8 |
| 2010/0227545 | A1* | 9/2010 | Frois | B01D 46/0005 |
| | | | | 454/358 |
| 2010/0285436 | A1* | 11/2010 | DeVore | G09B 23/06 |
| | | | | 434/188 |
| 2011/0017252 | A1 | 1/2011 | Braum et al. | |
| 2011/0126713 | A1* | 6/2011 | Legare | A62B 23/02 |
| | | | | 96/135 |
| 2012/0079945 | A1* | 4/2012 | Roberts | B01D 46/0038 |
| | | | | 96/222 |
| 2012/0180655 | A1 | 7/2012 | Law et al. | |
| 2014/0360143 | A1* | 12/2014 | Bush | B01D 46/0075 |
| | | | | 55/304 |

FOREIGN PATENT DOCUMENTS

| | | |
|---|---|---|
| CN | 2679567 Y | 2/2005 |
| CN | 201246859 Y | 5/2009 |
| CN | 201964563 U | 9/2011 |
| CN | 102384534 A | 3/2012 |
| CN | 202675518 U | 1/2013 |
| CN | 202746228 U | 2/2013 |
| CN | 204006375 U | 12/2014 |
| CN | 204006376 U | 12/2014 |
| CN | 204006377 U | 12/2014 |
| CN | 204006475 U | 12/2014 |
| CN | 204063427 U | 12/2014 |
| CN | 204084620 U | 1/2015 |
| DE | 2439899 A1 | 3/1976 |
| KR | 20100002099 U | 3/2010 |
| KR | 20120082827 A | 7/2012 |

OTHER PUBLICATIONS

Extended European Search Report for Application 14896570.0 dated May 24, 2017.

Office Action for Korean Application No. 10-2016-7036551 dated Sep. 5, 2018.

* cited by examiner

`US 10,429,093 B2`

AIR TREATMENT SYSTEM

CROSS-REFERENCE TO RELATED APPLICATION

This application is a national phase entry of PCT/CN2014/093283 filed on 8 Dec. 2014, which claims the benefit of priority of Chinese application No. 201410315032.0 filed on 3 Jul. 2014, the content of which is incorporated herein by reference in its entirety for all purposes.

TECHNICAL FIELD

The present invention relates to the field of air handling and, in particular, to an air handling system.

BACKGROUND OF THE INVENTION

Currently, combined air handling systems are increasingly present on the market. These combined air handling systems are typically composed of a combination of air handling devices with a single function. However, the connection structures of the current combined air handling systems are usually relatively complex, and it is very inconvenient for a user to assemble or disassemble the combined air handling system by himself, if necessary.

SUMMARY OF THE INVENTION

In view of this, an object of the present invention is to propose an air handling system. In order to provide a basic understanding of some aspects of the disclosed embodiments, a brief summary is given below. This summary is not an extensive overview, and is intended to neither identify key or critical elements nor delineate the scope of protection of such embodiments. Its sole purpose is to present some concepts in a simplified form as a prelude to the more detailed description that is presented later.

In some illustrative embodiments, an air handling system comprises a top cover, a base and at least one air handling device provided between the top cover and the base, wherein the top cover and the uppermost air handling device, the base and the lowermost air handling device, and the air handling devices are all connected to each other by means of magnetic attraction.

The technical effect in some illustrative embodiments is as follows: it is convenient to connect the various devices with each other by means of magnetic attraction, for easy assembly and disassembly.

To the accomplishment of the foregoing and related ends, one or more embodiments comprise the features hereinafter fully described and particularly pointed out in the claims. The following description and the accompany drawings set forth in detail certain illustrative aspects and are indicative only of a few of the various ways in which the principles of the various embodiments may be employed. Other advantages and novel features will become apparent from the following detailed description when considered in conjunction with the drawings, and the disclosed embodiments are intended to include all such aspects and their equivalents.

DETAILED DESCRIPTION OF THE INVENTION

The following description and the accompany drawings fully illustrate specific embodiments of the present invention so as to enable those skilled in the art to practice the same. Other embodiments may include structural, logical, electrical, procedural, and other changes. The embodiments represent only possible variations. Individual components and functions are optional, and the order of operations may vary, unless explicitly required. Portions and features of some embodiments may be included in or replace portions and features of other embodiments. The scope of the embodiments of the present invention encompasses the full scope of the claims, and all available equivalents of the claims. In this context, these embodiments of the present invention may be individually or collectively referred to by the term "invention" for convenience only, and if in fact more than one invention is disclosed, it is not intended to automatically limit that the application is within the scope of any single inventive or inventive concept.

Figure 1:
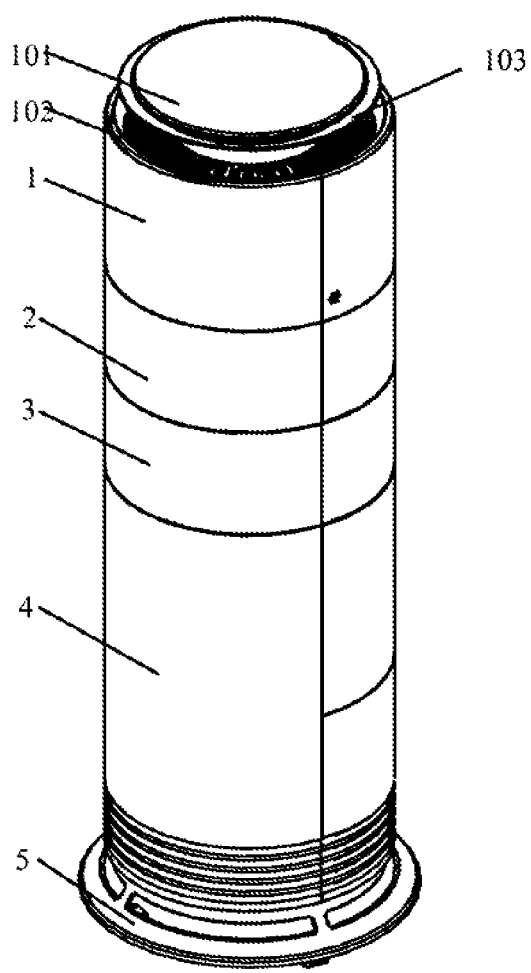
FIG. 1 is a perspective view of an air handling system in some embodiments.
Figure 2:
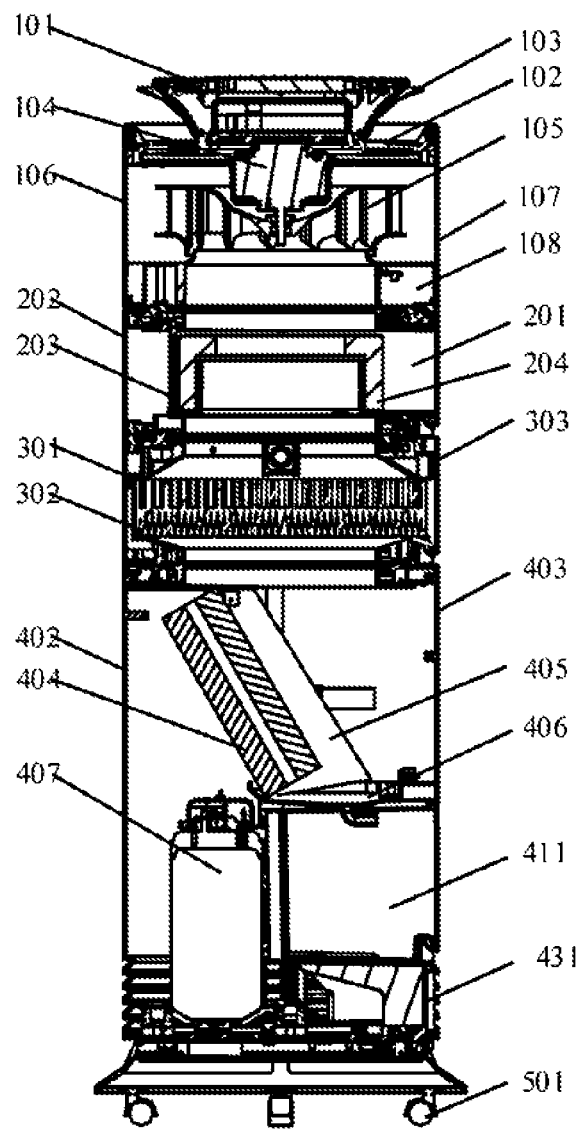
FIG. 2 is a sectional view of the air handling system in some embodiments.
Figure 3:
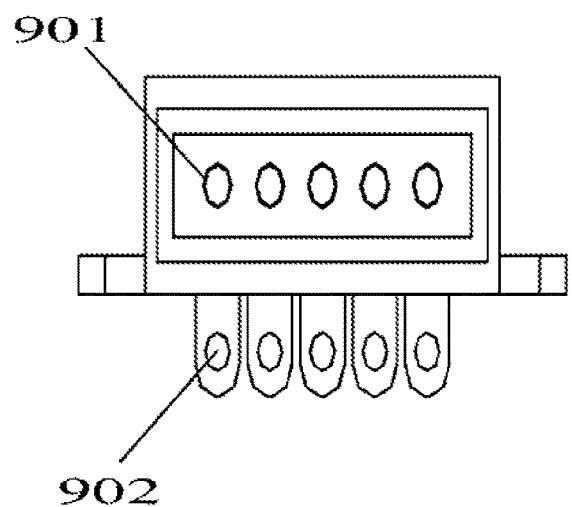
FIG. 3 is a first structural schematic view of a first terminal block in some embodiments.
Figure 4:
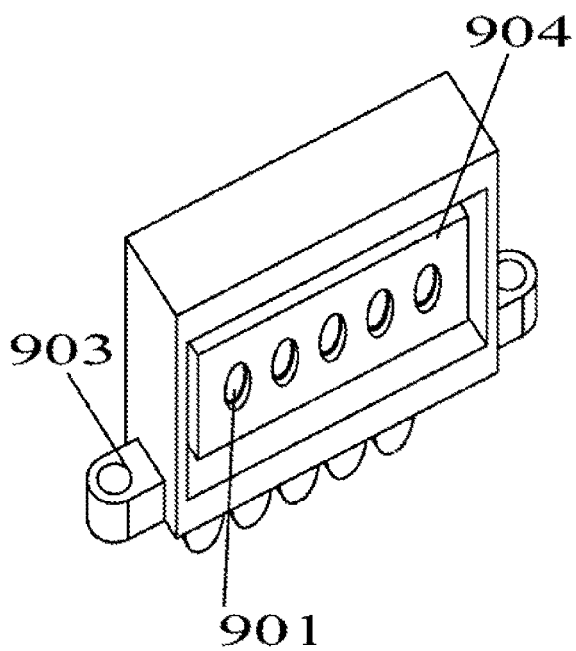
FIG. 4 is a second structural schematic view of the first terminal block in some embodiments.
Figure 5:
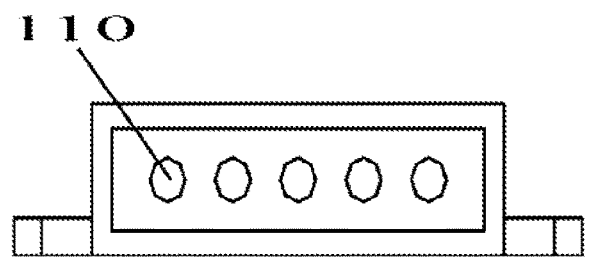
FIG. 5 is a first structural schematic view of a second terminal block in some embodiments.
Figure 6:
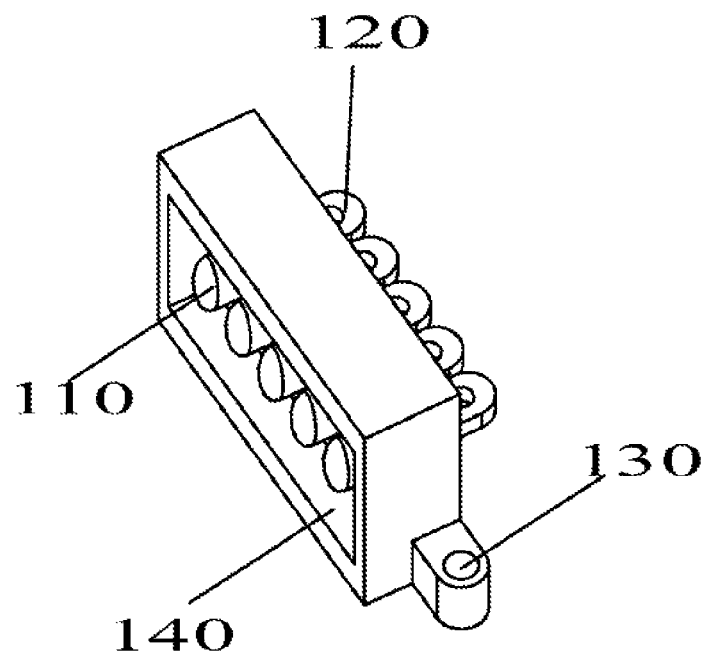
FIG. 6 is a second structural schematic view of the second terminal block in some embodiments.
Figure 7:
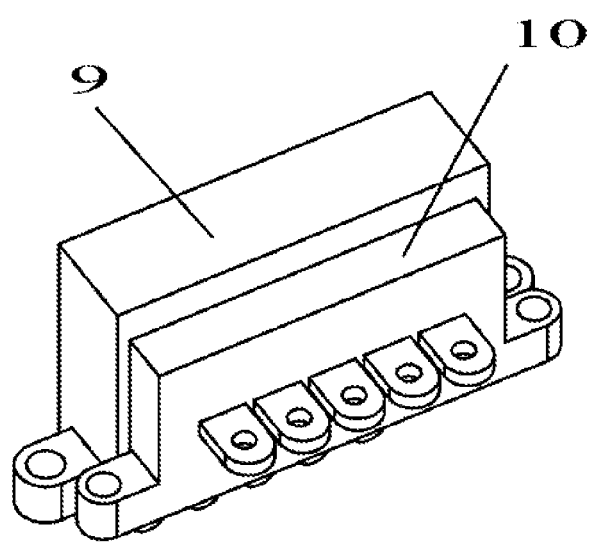
FIG. 7 is a structural schematic view of the first and second terminal blocks mating with each other in some embodiments.

Reference is made to FIGS. 1 and 2, which are perspective and sectional views, respectively, of an air handling system in some embodiments of the present invention.

The air handling system comprises a base 5 and one or more air handling devices disposed on the base 5. Each of the air handling devices comprises an air inlet, an air outlet, and a power-supply structure. In this embodiment, the air handling system has a dehumidifying device 4, a purifying device 3, and a humidifying device 2 which are sequentially assembled from the bottom to the top. It should be understood that the embodiments of the present invention are not intended to be limited thereto, other arrangements may be used, and modular devices having other functions may also be used.

In some illustrative embodiments, with the modular design of the air handling device, the choice of different modules achieves different functions, giving more choices to a user. The combination of the various modules adopts the upper-lower stacking method, which can fully save space.

In some illustrative embodiments, the base 5 comprises an air inlet, an air outlet, an external power source, and an output power-supply structure for powering the adjacent air handling device.

In some illustrative embodiments, the base 5 is connected to the adjacent air handling device by means of magnetic attraction or via connecting members. The adjacent air handling devices are connected to each other by means of magnetic attraction or via connecting members. The top cover 1 is connected to the adjacent air handling device by means of magnetic attraction or via connecting members.

In some illustrative embodiments, the various parts are conveniently connected by means of magnetic attraction or via connecting members.

Preferably, the base 5 is connected to the adjacent air handling device by means of magnetic attraction. The adjacent air handling devices are connected to each other by means of magnetic attraction. The top cover 1 is connected to the adjacent air handling device by means of magnetic attraction. The magnetic attraction is preferably carried out by providing at least one magnetic component on the bottom surface of the top cover 1, on the top and bottom surfaces of the air handling device, and on the top surface of the base 5, respectively. The magnetic component on the bottom surface of the top cover 1 positionally corresponds to the magnetic component on the top surface of the uppermost air handling device, and the polarities of the corresponding magnetic components are opposite. The magnetic component on the top surface of the base 5 positionally corresponds to the magnetic component on the bottom surface of the lowermost air handling device, and the polarities of the corresponding magnetic components are opposite. The magnetic component on the top surface of an air handling device corresponds to the magnetic component on the bottom surface of the adjacent air handling device, and the polarities of the corresponding magnetic components are opposite. The magnetic component may be arranged on the bottom surface of the top cover 1, on the top and bottom surfaces of the air handling device, and on the centre or circumference of the top surface of the base.

In some illustrative embodiments, the connection of the various modular devices of the air handling system by means of magnetic attraction makes both the structure of the air handling system and the installation process be simple. The user can complete the installation by himself without using any tool. In addition, the magnetic attraction also makes the structure of the installed air handling system be firm.

Preferably, the base 5 is connected to the adjacent air handling device via connecting members. The adjacent air handling devices are connected to each other via connecting members. The top cover 1 is connected to the adjacent air handling device via connecting members.

Preferably, the connecting members may be a slot and a jaw disposed on two adjacent faces, respectively. The jaw is snap-fitted into the slot, so that the various parts are connected together.

Preferably, the connecting members may also be of a guide groove and guide post structure. In some illustrative embodiments, the bottom of the top cover 1 and the bottom surface of the air handling device are respectively provided with at least one guide groove. The top surface of the air handling device and the top surface of the base 5 are respectively provided with at least one guide protrusion, and the guide groove and the guide protrusion which are provided on the adjacent two surfaces positionally correspond to each other such that the guide protrusion is inserted into the guide groove. The present application is not limited to this, it is also possible for the air handling device to be provided with a guide groove on one adjoining surface and with a guide post on the other adjoining surface, as long as the inserted connection of the guide groove and the guide post is achieved, and the types of terminal blocks on each surface are not limited. The guide groove and the guide post can not only realize the structural mating, but also play a guiding role when used together with other connecting structures. Preferably, the guide groove may be provided with an electrically conductive sheet, and the guide post is an electric conductor. This arrangement enables the guide groove and the guide post to perform a guiding function but also part of the electrical connection function.

In some illustrative embodiment, an air outlet of the top cover 1 is provided on the top surface of the top cover 1, and the bottom surface of the top cover 1 is provided with an air inlet. The air inlet of the top cover 1 is connected to the air outlet of the adjacent air handling device. The air inlet of the base 5 is provided on the bottom surface of the base 5, and the air outlet of the base 5 is provided on the top surface of the base 5. When multiple air handling devices are connected, the air outlet of each of the air handling devices is connected to the air inlet of the adjacent air handling device.

In some illustrative embodiments, the air inlet of the air handling device adjacent to the base 5 has two arrangements as follows:

In some illustrative embodiments, the air inlet of the air handling device adjacent to the base 5 is provided on a side wall of the air handling device. The orientation of the air outlet of the top cover 1 and of the air inlet of the air handling device adjacent to the base 5 both point to the surroundings in an unobstructed manner. Preferably, the bottom surface of the air handling device may be not provided with the air inlet, and the air duct between the air handling device and the base 5 is not provided; in this case, the wind enters from the air inlet of the air handling device and would not enter from the air inlet of the base 5. Preferably, the bottom surface of the air handling device may be provided with the air inlet, and the air duct between the air handling device and the base 5 is provided; in this case, the wind can enter from both the air inlet of the air handling device and the air inlet of the base 5.

In some illustrative embodiments, the air inlet of the air handling device adjacent to the base 5 is provided on the bottom surface of the air handling device. The air outlet of the base 5 is connected to the air inlet of the adjacent air handling device. The orientation of the air outlet of the top cover 1 and of the air inlet of the base 5 both point to the surroundings in an unobstructed manner. In this case, the wind enters from the air inlet of the base. In this solution, the air handling device adjacent to the base 5 needs to have a sufficient strength, and is preferably of a metal material.

In some illustrative embodiments, each of the air outlets may be a grid-like air inlet or a hole-shaped air inlet.

Reference is made to FIGS. 3 to 7, which are respectively first and second structural schematic views of a first terminal block, first and second structural schematic views of a second terminal block, and a structural schematic view of the first and second terminal blocks mating with each other in some embodiments of the present invention.

In some illustrative embodiments, the top cover 1, the base 5 and the air handling devices of the air handling system are provided with connectors which can be used as the structure of a power source connection interface and a communication connection interface for the top cover 1, the base 5 and the air handling devices. The connector comprises a first terminal block 9 and a second terminal block 10. The first terminal block 9 has a boss 904 on a side wall thereof, and at least one connecting hole 901 is provided on the boss 904. In this embodiment, a side wall of the second terminal block 10 is provided with a groove 140 which matches with the boss 904, and at least one connecting post 110 which matches with the connecting hole 901 is provided in the groove 140. When the first terminal block 9 mates with the second terminal block 10, the boss 904 is embedded into the groove 140 and is snap-fitted with the groove 140. When the first terminal block 9 mates with the second terminal block 10, the connecting post 110 is inserted into the connecting hole 901 so that the outer surface of the connecting post 110 makes contact with the inner surface of the connecting hole 901. At least one first terminal 902 electrically connected to the connecting hole 901 is provided on a side wall of the first terminal block 9 parallel to the axial direction of the connecting hole 901. At least one first fixing seat 903 is respectively provided on opposite side walls of the first terminal block 9 perpendicular to the side wall on which the boss 904 is provided. At least one second terminal 120 electrically connected to the connecting post 110 is provided on a side wall of the second terminal block 10 opposite to the groove 140 on which the connecting post 110 is provided. At least one second fixing seat 130 is respectively provided on opposite side walls of the second terminal block 10 perpendicular to the side wall on which the groove 140 is provided. The inner wall or the inner bottom wall of the connecting hole 901 may be of a material having an electrically conductive function, or may be a mechanism having a communication pin. Preferably, a functional contact element may be specially provided in the connecting hole 901. The functional contact element is an electrically conductive sheet or a communication pin. When the first terminal block 9 mates with the second terminal block 10, the outer surface of the connecting post 110 makes contact with the functional contact element. The present application is such that the air handling device is provided with a first terminal block 9 on one adjoining surface and with a second terminal block 10 on the other adjoining surface, as long as the inserted connection of the first terminal block 9 and the second terminal block 10 is achieved, and the types of terminal blocks on each surface are not limited. The movement to achieve the mating of wires may be a linear movement, or may be a rotational movement. In addition, in accordance with this mating method, different numbers of pairs of terminals can be designed according to the number of the wires (of strong or weak currents) required to mate.

The following describes the structures of the various parts of the air handling system by way of example. It should be understood that the structures of the various parts are not limited to the following embodiments.

Figure 8:
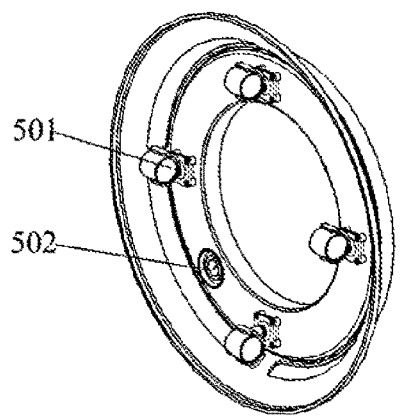
FIG. 8 is a first structural schematic view of a base in some embodiments.
Figure 9:
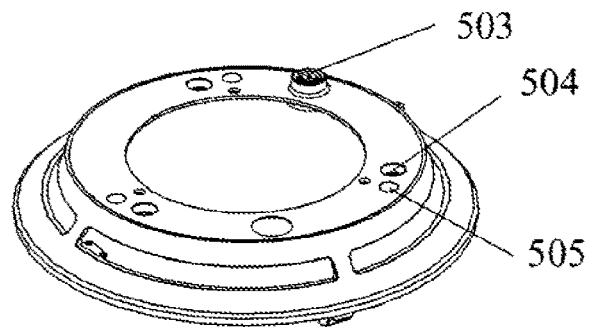
FIG. 9 is a second structural schematic view of the base in some embodiments.

Reference is made to FIGS. 8 and 9, which are respectively first and second structural schematic views of a base in some embodiments of the present invention.

In some illustrative embodiments, an omni-directional wheel 501 is provided beneath the bottom surface of the base 5 to facilitate movement of the air handling system.

In some illustrative embodiments, the upper surface of the base 5 is provided with a trench. Preferably, the trench is of a circular ring structure concentric with the base. The trench can be used for wire coiling to facilitate the storage of wires.

In some illustrative embodiments, the power-supply output structure of the base 5 is specified as a base power source mating interface 503. The base 5 may also comprise a base communication mating interface for communication connection. Of course, the base power source mating interface 503 and the base communication mating interface may be integrated into one interface. The base 5 may also comprise a base power source output interface 502 for connection to an external power source. The power source mating interface 503, the base communication mating interface and the base power source output interface 502 employ the structure of the first terminal block or the second terminal block of the connector as described above.

Figure 10:
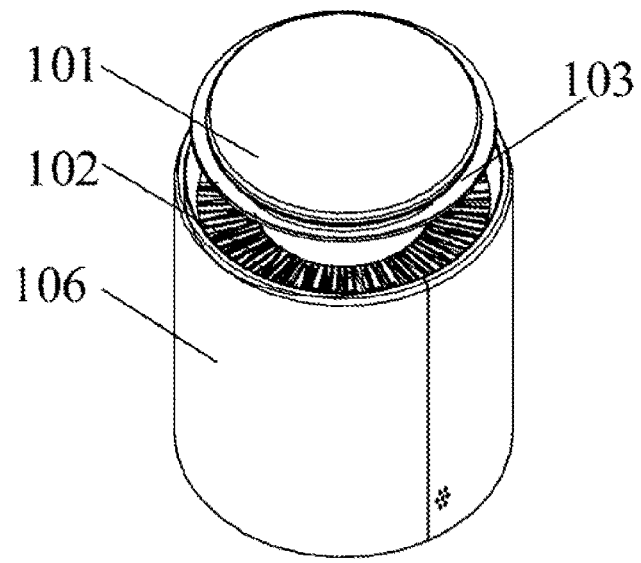
FIG. 10 is a first structural schematic view of a top cover in some embodiments.
Figure 11:
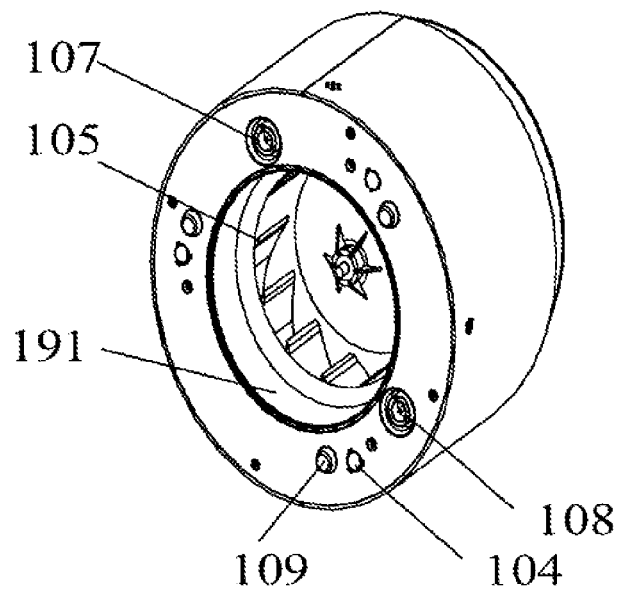
FIG. 11 is a second structural schematic view of the top cover in some embodiments.
Figure 12:
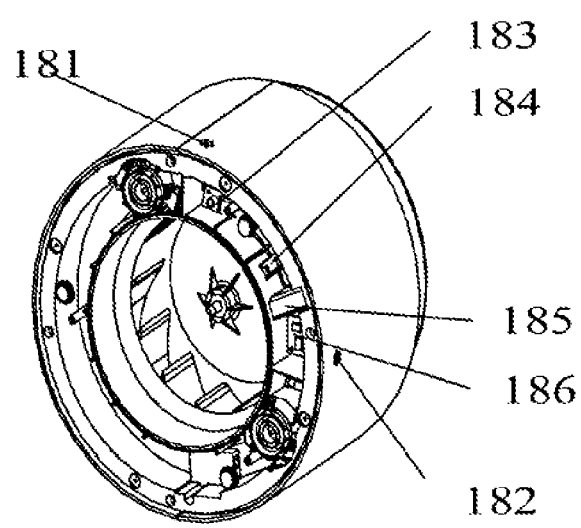
FIG. 12 is a third structural schematic view of the top cover in some embodiments.
Figure 13:
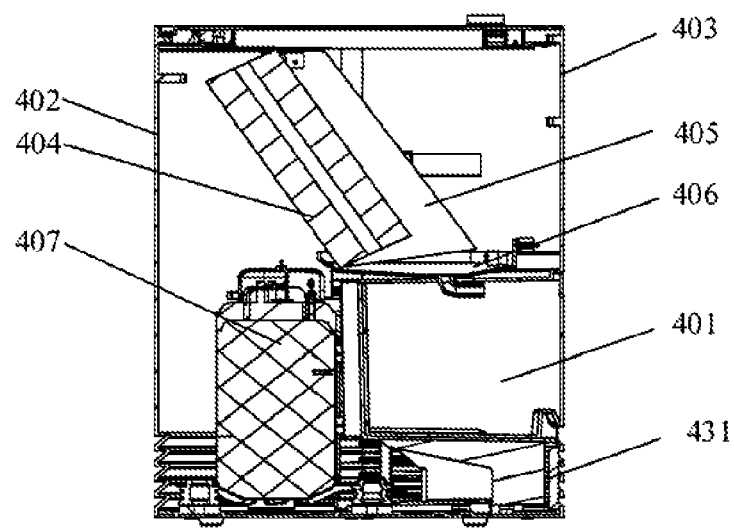
FIG. 13 is a first structural schematic view of a dehumidifying device in some embodiments.
Figure 14:
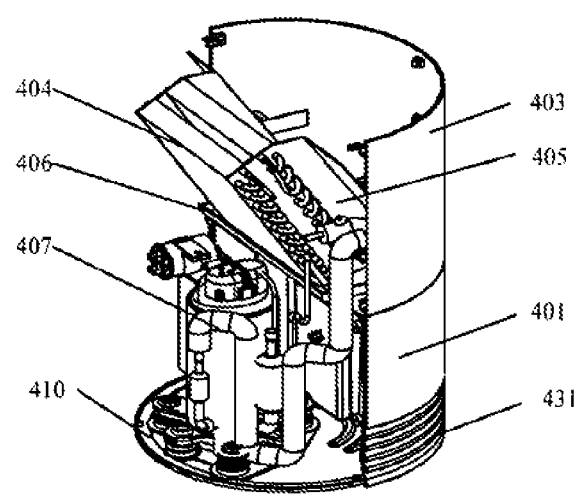
FIG. 14 is a second structural schematic view of the dehumidifying device in some embodiments.

Reference is made to FIGS. 10-12, which are respectively first, second and third structural schematic views of a top cover in some embodiments of the present invention.

In some illustrative embodiments, the air handling system further comprises a top cover 1, which is disposed on the one or more air handling devices. The top cover 1 comprises an air inlet 191, an air outlet 102, and a power-supply input structure for receiving the power supplied from the adjacent air handling device. The power-supply input structure is provided on the bottom surface of top cover 1. The power-supply input structure is specified as top cover power source mating interface 107. The air handling system may further comprise a top cover communication mating interface 108 provided on the bottom surface of the top cover for communication connection. Of course, the top cover power source mating interface 107 and the top cover communication mating interface 108 may be integrated into one interface. The top cover source mating interface 107 and the top cover communication mating interface 108 employ the structure of the first terminal block or the second terminal block of the connector as described above. The top cover 1 is further provided with a top cover magnet 109 and a guide post 104 on the bottom surface thereof. The top cover magnet 109 is the aforementioned magnetic component, and the guide post 104 is of the aforementioned guide post structure.

In some illustrative embodiments, a side wall of the top cover 1 comprises an inner wall and an outer wall, and a spacing is arranged between the inner wall and the outer wall. The top cover 1 is further provided with a detection unit. The detection unit comprises a detection air inlet 181, a detection air outlet 182, a detection fan 184 and sensors. The detection air inlet 181 and the detection air outlet 182 are respectively provided on the surface of the outer wall 106 of the top cover. The detection fan 184 and the sensors are provided in the spacing between the detection air inlet 181 and the detection air outlet 182. In this embodiment, the sensors comprise a VOC (volatile organic compounds) sensor 183, a PM2.5 detection device 185, and a temperature and humidity sensor 186, and the like. It should be understood that the present invention is not limited to this, and the sensors may be other types of sensors for detecting air indicators. In some illustrative embodiments, the quality of the air can be detected by using the detection unit.

In some illustrative embodiments, a motor 104 is further provided in the top cover 1. The motor 104 is used to power the air handling system.

In some illustrative embodiments, a protrusion is provided on the top surface of the top cover 1, and a display screen 101 is provided on the surface of the protrusion. The display screen 101 serves as a human-computer interaction interface for displaying the current operating state, the operation being performed by the user, and the like. The outer periphery of the display screen is provided with a circular indicator lamp strip, which may serve as an indication of machine operation, stop, or malfunction. The indicator lamp strip can also be used to indicate air quality, for example, different colours of the indicator lamp strip represent different air quality levels.

In addition to the basic controls, the top cover 1 can also be equipped with an infrared transceiver for controlling other household appliances in some illustrative embodiments.

Reference is made to FIGS. 13-17, which are respectively first through fifth structural schematic views of a dehumidifying device in some embodiments of the present invention.

In some illustrative embodiments, the air handling device may be a dehumidifying device 4. The dehumidifying device 4 comprises a heat exchanger 404, a water receiving tray 406, and a water tank 401. The water receiving tray 406 is located at the top of the water tank 401, and at least one water outlet hole, which is in communicating with the water tank 401, is provided on the water receiving tray 406. The angle between the heat exchanger 404 and the plane where the water receiving tray 406 is located is not equal to 90 degrees. An extension line of the lower end of the heat exchanger 404 in the axial direction of the dehumidifying device intersects the plane where the water receiving tray 406 is located.

In some illustrative embodiments, the heat exchanger 404 is not disposed horizontally or vertically above the water receiving tray 406 as in the prior art, but the heat exchanger 404 is disposed obliquely above the water receiving tray 406, so that the condensed water generated when the heat exchanger 404 is operated may flow into the water receiving tray 406 along the bottom end of the heat exchanger 404 and then flow into the water tank 401 from the water receiving tray 406. Optionally, a hole in communication with the water tank 401 is provided on the water receiving tray 406, so that condensed water flows into the water tank 401 through the hole. Optionally, the hole of the water receiving tray 406 for draining the condensed water may also be directly connected to a water outlet pipe such that the condensed water is discharged from the dehumidifying device through the water outlet pipe.

In some illustrative embodiments, the dehumidifying device comprises an air inlet 431 and an air outlet 432. The air outlet 432 is provided on a dehumidifying top cover 408 of the dehumidifying device. In this embodiment, the dehumidifying device 4 is arranged to be connected to the base 5, so that the air inlet 431 has two arrangements as described above. The air outlet 431 is provided on a side wall of the dehumidifying device and/or a dehumidifying chassis 410.

In some illustrative embodiments, a fixing plate 405 of the heat exchanger 404 is fixedly connected to the side wall of the dehumidifying device. A housing of the dehumidifying device comprises a front dehumidifying housing 402, a rear dehumidifying housing 403, a dehumidifying top cover 408 and a dehumidifying chassis 410, and the fixing plate 405 of the heat exchanger 404 is fixed to the front dehumidifying housing 402. Optionally, the heat exchanger 404 is fixedly connected to the fixing plate 405 of the heat exchanger 404 via bolts.

In some illustrative embodiments, both the heat exchanger 404 and the water receiving tray 406 are provided within the housing. The water tank 401 is separate from the housing, and a groove for having the water tank 401 placed therein is provided on the machine housing, such that the water tank 401 can be freely detached from the housing of the dehumidifying device for the convenience of the user.

The front dehumidifying housing 402 and the rear dehumidifying housing 403 may be fixedly connected via a slot or a bolt or the like, and the rear dehumidifying housing 403 is provided with a groove for having the water tank 401 placed therein. The water receiving tray 406 is placed on the top of the groove of the rear dehumidifying housing 403. The water receiving tray 406 may be integrated with or separate from the rear dehumidifying housing 403. Optionally, a slide rail may be provided on the groove and a slideway may be provided in the corresponding position on the bottom of the water tank 401 to facilitate the removal of the water tank 401 more quickly and effortlessly.

In some illustrative embodiments, the air inlet 431 may be disposed on at least a portion of a side wall of the machine housing from the bottom of the machine housing to the bottom of the water tank 401. As shown in FIG. 12, the air inlet 431 is disposed on the entire side wall of the machine housing from the bottom of the machine housing to the bottom of the water tank 401.

Optionally, the air inlet 431 may be disposed on part of the side wall, for example, only the front dehumidifying housing 402 or the rear dehumidifying housing 403 is provided with the air inlet 431. Of course, the air inlet 431 may also be provided on the side wall of the dehumidifying device above the water tank 401.

In some optional embodiments, the dehumidifying device further comprises a compressor 407 and an electrical cabinet. The compressor 407 and the electrical cabinet are located at the bottom of the dehumidifying device, as shown in the figure, and the compressor 407 is generally bulky and is thus placed in the space enclosed by the front dehumidifying housing 402. In order to save space, the electrical cabinet is placed at the bottom of the space enclosed by the rear dehumidifying housing 403, and a groove for having the water tank 401 placed therein is provided on the rear dehumidifying housing 403, such that a certain space is provided from the groove to the dehumidifying chassis 410, and the electrical cabinet is placed in the space. The electrical cabinet is used to store a circuit board.

In some optional embodiments, a lower power source interface 412 and a lower communication interface 411 are provided on the dehumidifying top cover 408. A corresponding upper power source interface 413 is further provided on the humidifying chassis. Further, the lower power source interface 412 and the lower communication interface 411 may be the same interface. The lower power source interface 412, the lower communication interface 411 and the upper power source interface 413 may employ the structure of the first terminal block or the second terminal block of the connector as described above.

In some optional embodiments, the dehumidifying device is further provided with a connecting structure which is connected to the other devices as described above; the connecting structure may be a connecting member structure as described above, or a guiding structure as described above, such as a guide groove and a guide post, the guide post and the corresponding guide groove of the respective devices being arranged to mate with each other. A guide groove 414 and a guide post 415 are respectively provided on the dehumidifying top cover 408 and the dehumidifying chassis 410. In addition, a lower magnet 416 and an upper magnet 413 may be also respectively provided on the dehumidifying top cover 408 and the dehumidifying chassis 410, so that the dehumidifying device is connected to other devices by means of attraction. The lower magnet 416 and the upper magnet 413 may be the aforementioned magnetic components.

In some illustrative embodiments, a lower power source interface 412 and a lower communication interface 411 are provided on the dehumidifying top cover 408. A corresponding upper power source interface 413 is further provided on the dehumidifying chassis 410. Each of the interfaces may be the connector structure as described above, and is arranged to correspond to the position of the corresponding interface of the other devices.

In some illustrative embodiments, the heat exchanger 404 can also be placed horizontally in the dehumidifying device, since the area where condensed water is dropped from the heat exchanger when the heat exchanger 404 is placed horizontally is relatively large, the size of the water receiving tray 406 is correspondingly increased in accordance with the horizontal area of the heat exchanger 404.

With the dehumidifying device of the above embodiment, the following effects can be achieved: the size of the dehumidifier is reduced; the area of the water receiving tray is no longer restricted by the size of the heat exchanger; and the heat exchange efficiency is improved.

Figure 18:
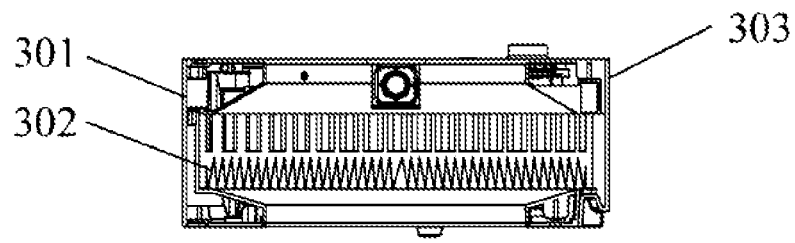
FIG. 18 is a first schematic view of a purifying device in some illustrative embodiments.
Figure 19:
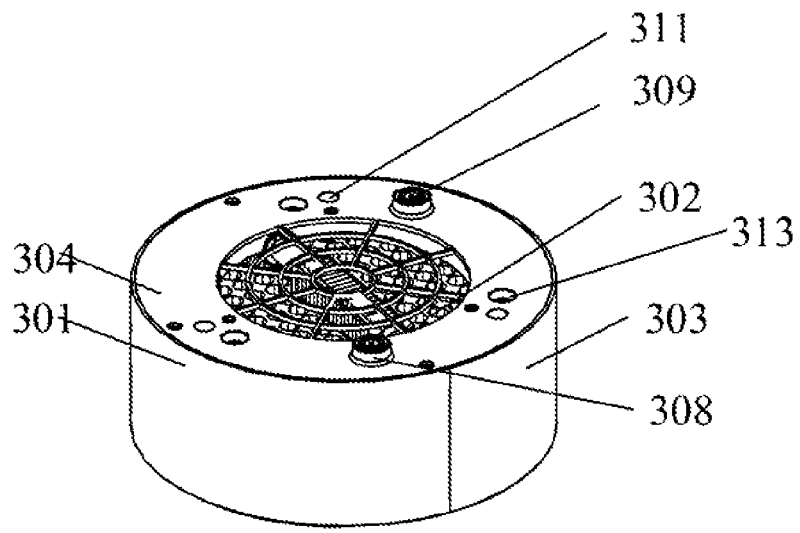
FIG. 19 is a second schematic view of the purifying device in some illustrative embodiments.
Figure 20:
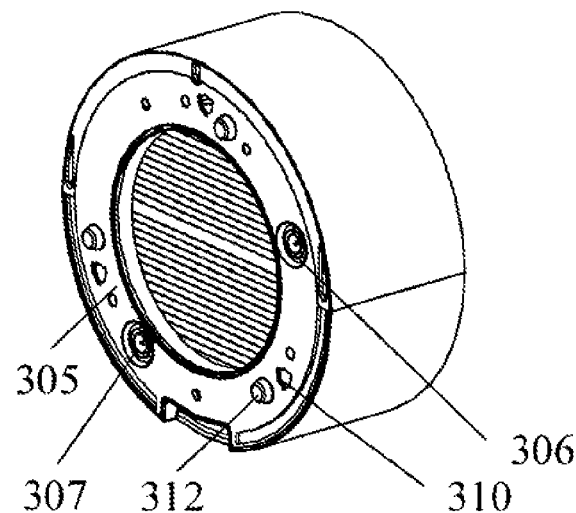
FIG. 20 is a third schematic view of the purifying device in some illustrative embodiments.
Figure 21:
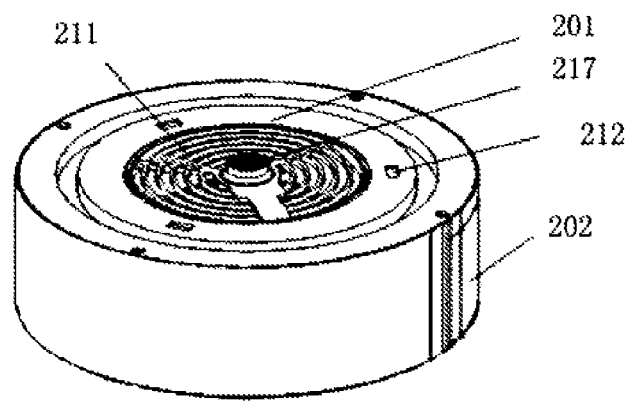
FIG. 21 is a first schematic view of a humidifying device in some illustrative embodiments.
Figure 22:
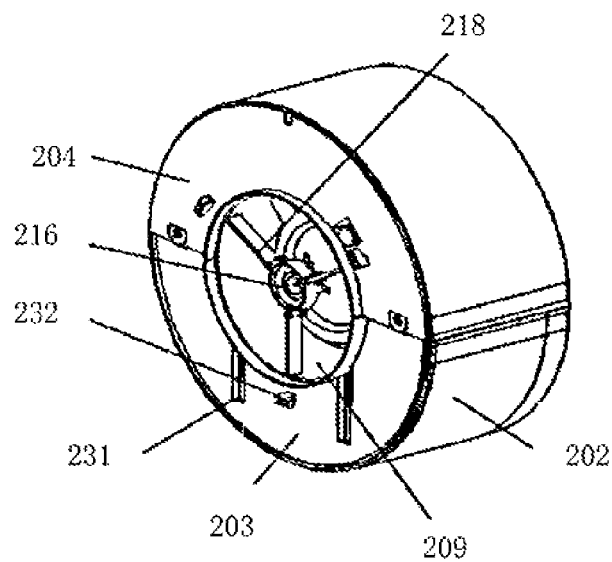
FIG. 22 is a second schematic view of the humidifying device in some illustrative embodiments.
Figure 23:
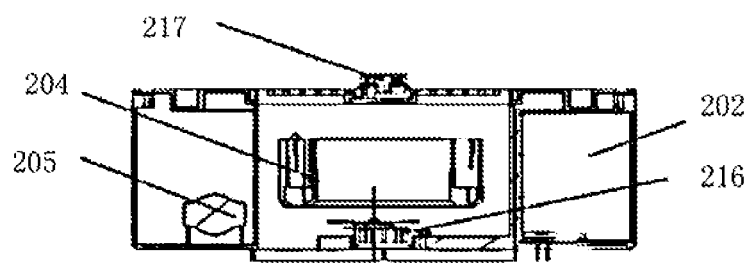
FIG. 23 is a third schematic view of the humidifying device in some illustrative embodiments.
Figure 24:
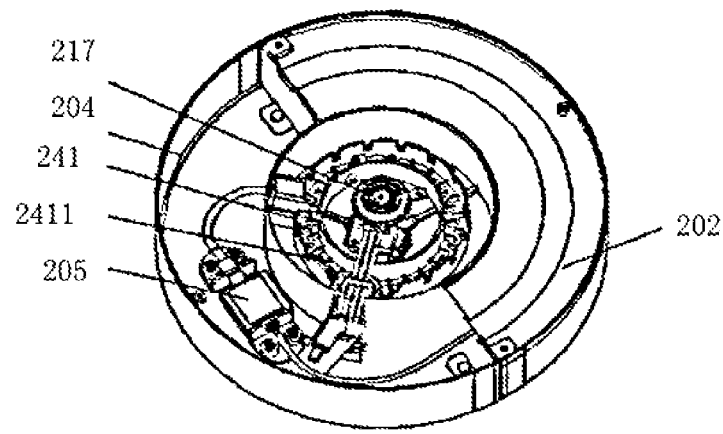
FIG. 24 is a fourth schematic view of the humidifying device in some illustrative embodiments.
Figure 25:
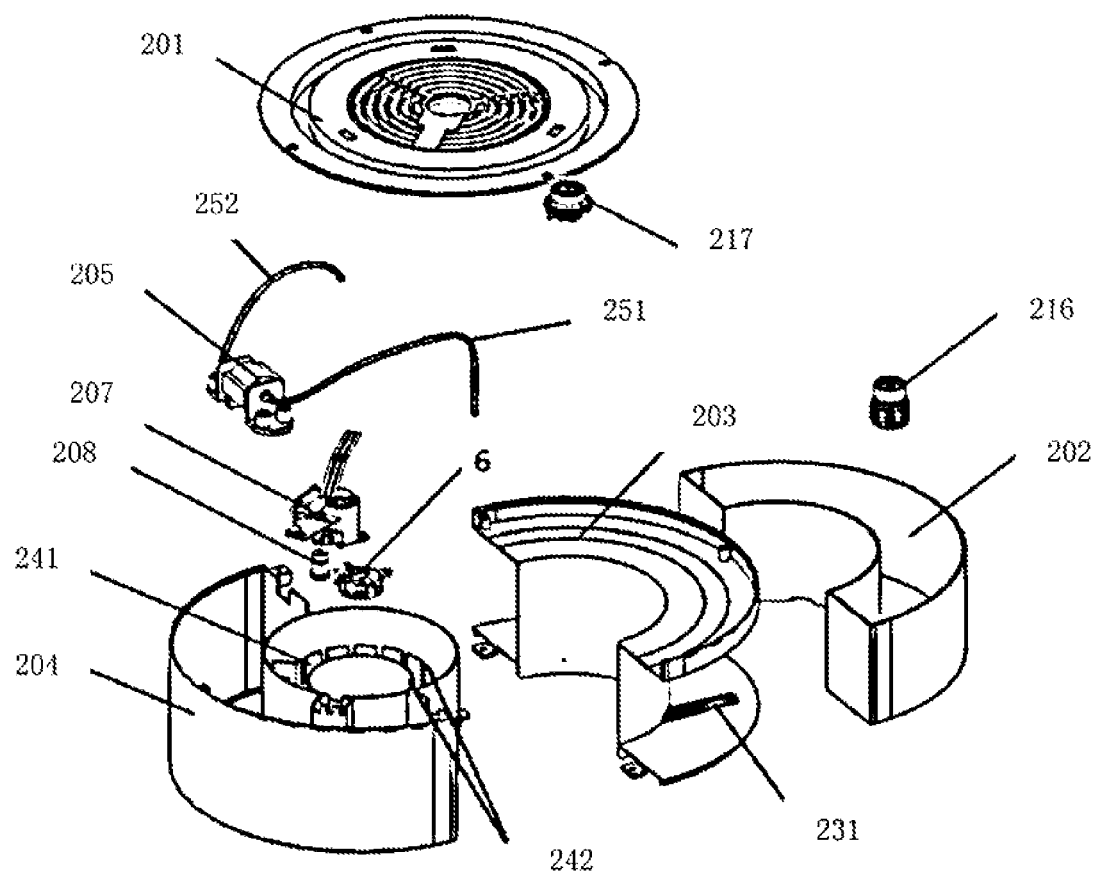
FIG. 25 is a fifth schematic view of the humidifying device in some illustrative embodiments.
Figure 26:
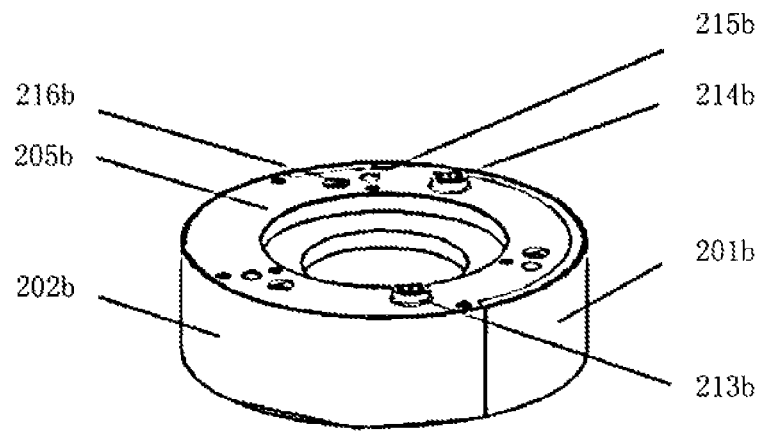
FIG. 26 is a first schematic view of a further humidifying device in some illustrative embodiments.
Figure 27:
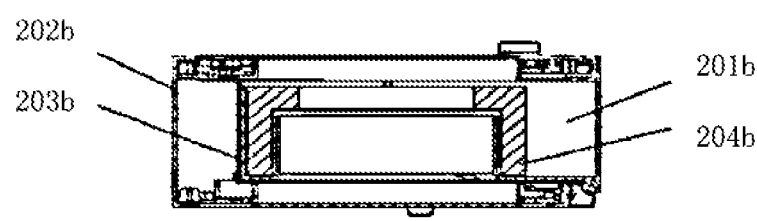
FIG. 27 is a second schematic view of the further humidifying device in some illustrative embodiments.

Reference is made to FIGS. 18-20, which are respectively first through third schematic views of a purifying device in some illustrative embodiments of the present invention.

The purifying device 3 comprises a front purifying housing 301, a purifying module 302, a rear purifying housing 303, a purifying top cover 304 provided above the purifying device 3, and a purifying disk 305 provided below the purifying device 3. The purifying module 302 of the purifying device 3 is fixed to the rear purifying housing 303. The rear purifying housing 303 can be pulled during replacement, so that the purifying module 302 can be removed. The purifying device 3 may comprise, in addition to the purifying module 302, a germicidal UV lamp or a nano-copper or -silver sterilization filter, anion, fragrance and the like.

The purifying device 3 is further provided with an upper power source mating interface 306, an upper mating interface 307, a lower power source mating interface 308 and a lower communication mating interface 309 employing the structure of the first terminal block or the second terminal block of the connector as described above. The purifying device 3 is further provided with an upper magnet 310 and a lower magnet 311 employing the structure of the magnetic components as described above. The purifying device 3 is further provided with the structure of a guide post 312 and a guide groove 313 as described above.

Reference is made to FIGS. 21-25, which are respectively first through fifth schematic views of a humidifying device in some illustrative embodiments of the present invention.

In some illustrative embodiments, the humidifying device comprises a water tank 202 for storing water, a water pump 205, and a water channel 241 connected to the water pump 205 via a lower water pipe 252. The water pump 205 is connected to the water tank 202 via an upper water pipe 251. The water pump 205 pumps the water from the water tank 202 to the water channel 241.

In this embodiment, the humidifying device is a pure humidifying device which pumps water from the water tank 202 to the water channel 241 by using the water pump 205 and diffuses the water in the water channel 241 into the air by means of natural evaporation, so as to achieve the effect of humidification; in addition, a water level monitoring device may be provided in the water channel 241 to detect the level of water in the water channel 241 in real time, when the water level is lower than a set water level, the water pump 205 is started to pump water, and when the water level reaches the set water level, the water pump 205 is stopped.

Figure 15:
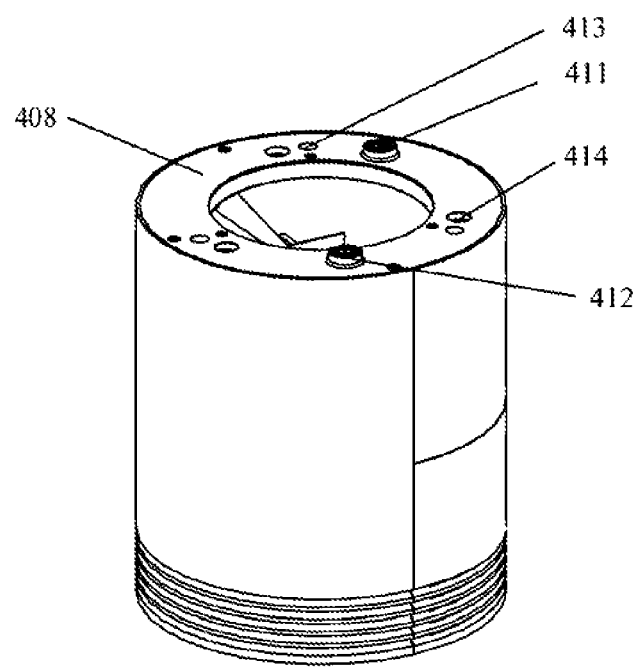
FIG. 15 is a third structural schematic view of the dehumidifying device in some embodiments.
Figure 16:
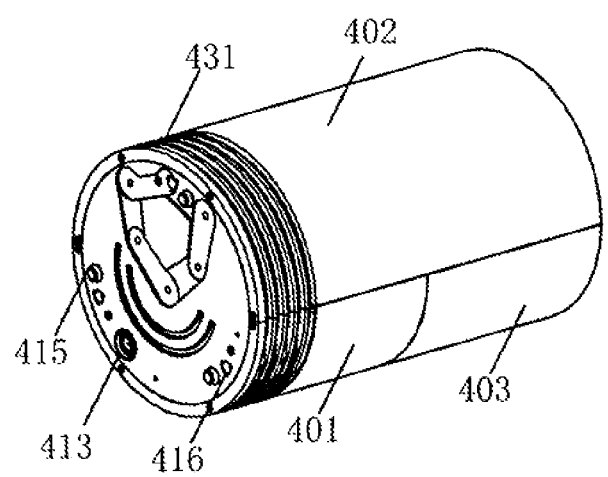
FIG. 16 is a fourth structural schematic view of the dehumidifying device in some embodiments.
Figure 17:
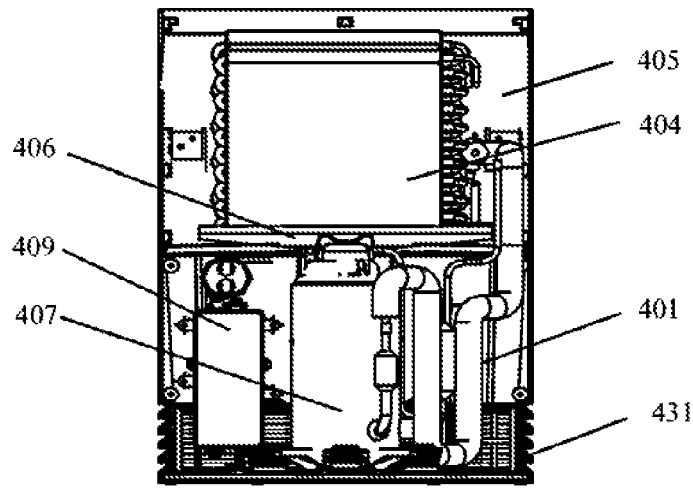
FIG. 17 is a fifth structural schematic view of the dehumidifying device in some embodiments.

In some illustrative embodiments, the water channel 241 is provided with a water retaining sheet 2411 therein. The height of the water retaining sheet 2411 is smaller than the height of an outer wall 2412 of the water channel 241. The water retaining sheet 2411 functions to slow down the flow rate of the water when the water pump 205 pumps the water into the water channel 241, so as to prevent the water from spilling out of the water channel 241. The shape of the water retaining sheet 2411 may be as shown in FIG. 15, and the height of the water retaining sheet 2411 is lower than that of the outer wall 2412 of the water channel 241, and is designed to be serrated to achieve the effect of slowing water flow.

In some illustrative embodiments, a water filter 206 is further provided within the water tank 202. The upper water pipe 251 extends into the water tank 202 and is connected to the water filter 206. The water filter 206 functions to purify the water so that the water entering the water channel 241 is purified by the water filter 206 to remove undesirable substances such as impurities and bacteria in the water.

In some illustrative embodiments, a connecting seat 208 for fixing the lower water pipe 252 of the water pump 205 is provided within the water channel 241, so that the lower water pipe 252 does not move due to water flow during pumping of water.

In some illustrative embodiments, the water pump 205 and the water channel 241 are placed inside a housing of the humidifying device. The water tank 202 is separate from the housing of the humidifying device, and the humidifying housing is provided with a groove for having the water tank placed therein. The housing of the humidifying device comprises a humidifying top cover 201, a front humidifying housing 204, and a rear humidifying housing 203. The water pump 205 and the water channel 241 are both disposed within front humidifying housing 204. The rear humidifying housing 203 is connected together with the front humidifying housing 204 via connecting members such as bolts or slots. The humidifying top cover 201 is fastened to the upper surfaces of the above two housings and is fixedly connected together therewith to form the housing of the humidifying device. The rear humidifying housing 203 is provided with a groove the structure of which matches with the water tank 202, so that the water tank 202 can be freely detached from the housing of the humidifying device for the convenience of the user.

Optionally, a slide rail 231 may be provided at the bottom of the groove and a slideway may be provided in the corresponding position on the bottom of the water tank 202 to facilitate the removal of the water tank 202 more quickly and effortlessly.

In some illustrative embodiments, the humidifying device comprises an air duct penetrating through the humidifying device. The water channel 241 surrounds the air duct.

The specific arrangement may be as follows: after the front humidifying housing 204 mates with the rear humidifying housing 203, there is an air inlet 209 dedicated for ventilation at the bottom of the humidifying device. The water channel 241 has a hollow design that surrounds the air duct and increases the rate of water evaporation around the air duct (i.e., the water channel 241) when the air passes through the water channel 241. An air outlet 211 for ventilation (from which water vapour is evaporated outwardly) is provided on the upper surface of the humidifying device (i.e., the humidifying top cover 201).

Further, the air duct runs through the centre of the humidifying device. The air duct runs through the centre of the humidifying device and is also located in the centre of the water channel 241.

Since the air duct needs to pass through the whole humidifying device, the whole humidifying device can be regarded as a ring-like structure (in cross section), the shapes of the inner and outer rings may be the same or different, and the inner or outer ring may be of a round, square or triangular structure. The humidifying device is preferably concentrically ring-shaped, and this design is more conducive to ventilation and evaporation of the water vapour.

Optionally, the shape of the inner ring defines the structure of the air duct, and the longitudinal section of the air duct may be rectangular or be of other structures such as a trapezoid; for a better understanding, if the longitudinal section of the air duct is rectangular, it is approximately understood that the air duct is of a cylinder or cubic structure, and if the longitudinal section is a trapezoidal, the air duct may be of a nearly circular cone structure.

In some illustrative embodiments, the humidifying device comprises a power-supply structure. The power-supply structure comprises a power-supply input structure for receiving an external power-supply and a power-supply output structure for supplying power to the outside. The power-supply input structure and the power-supply output structure may be specified as power source interfaces. Optionally, a power source interface is respectively provided at the top and bottom of the housing of the humidifying device. A communication interface may also be provided at the top and bottom of the housing of the humidifying device. Further, the humidifying top cover 201 is provided with a combined power source and communication interface, that is, a lower combined power source and communication interface 217, and an upper combined power source and communication interface 216 is provided at the bottom of the humidifying device; of course, the power source interface and the communication interface may be two separate interfaces, and the positions can also be correspondingly arranged according to the positions of the interfaces of other devices which mate with the humidifying device. The power source interface, the combined power source and communication interface and the communication interface may employ the structure of the first terminal block or the second terminal block of the connector as described above.

The overall circuit is located in the centre of the water channel 241, coinciding with the position of the air duct, the lower combined power source and communication interface 217 is connected to a circuit connecting member 207 on the humidifying top cover 201, and the circuit connecting member 207 is then connected to the upper combined power source and communication interface 216 at the bottom of the humidifying device.

In order to fix in the air duct the lower combined power source and communication interface 217, the circuit connecting member 207 and the upper combined power source and communication interface 216 at the bottom of the humidifying device, the present invention is provided with a fixing frame 218 at the bottom of the humidifying device for fixedly connecting the components described above.

The humidifying device is provided with a connecting structure which is connected to the other devices described above, a slot 212 may be provided on the humidifying top cover 201 and a jaw 232 on the housing at the bottom of the humidifying device, so that the humidifying device is connected to the corresponding slot or jaw of the other device in a mating manner. Further, if the connection mode is snap-fit, magnet components may be attached to the humidifying device and other devices to make the mutual attraction between the devices be secure and facilitate mounting; of course, the magnet components may also be designed separately from the connection structure so that the humidifying device is connected to the other devices by means of attraction.

With the above embodiment, the following effects can be achieved: a simple structure, a good safety performance, no "white-powder" pollution, and easy to clean the device; and the principle of natural evaporation is adopted, such that the present invention is more green and healthy.

Reference is made to FIGS. 26-29, which are respectively first through fourth schematic views of a further humidifying device in some illustrative embodiments of the present invention.

In some optional embodiments, the humidifying device comprises an air duct penetrating axially through the humidifying device, a water tank 201b for storing water, and a filter element 204b disposed in the water tank, wherein the water tank 201b surrounds the air duct.

Figure 28:
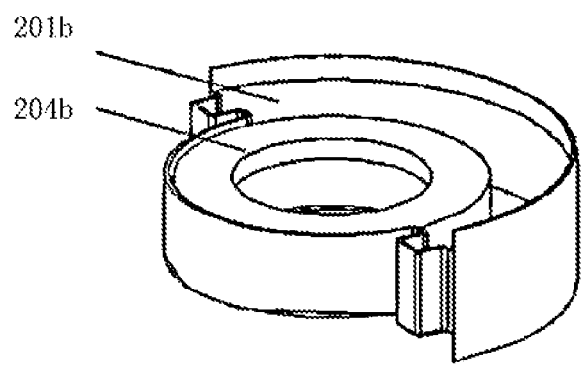
FIG. 28 is a third schematic view of the further humidifying device in some illustrative embodiments.
Figure 29:
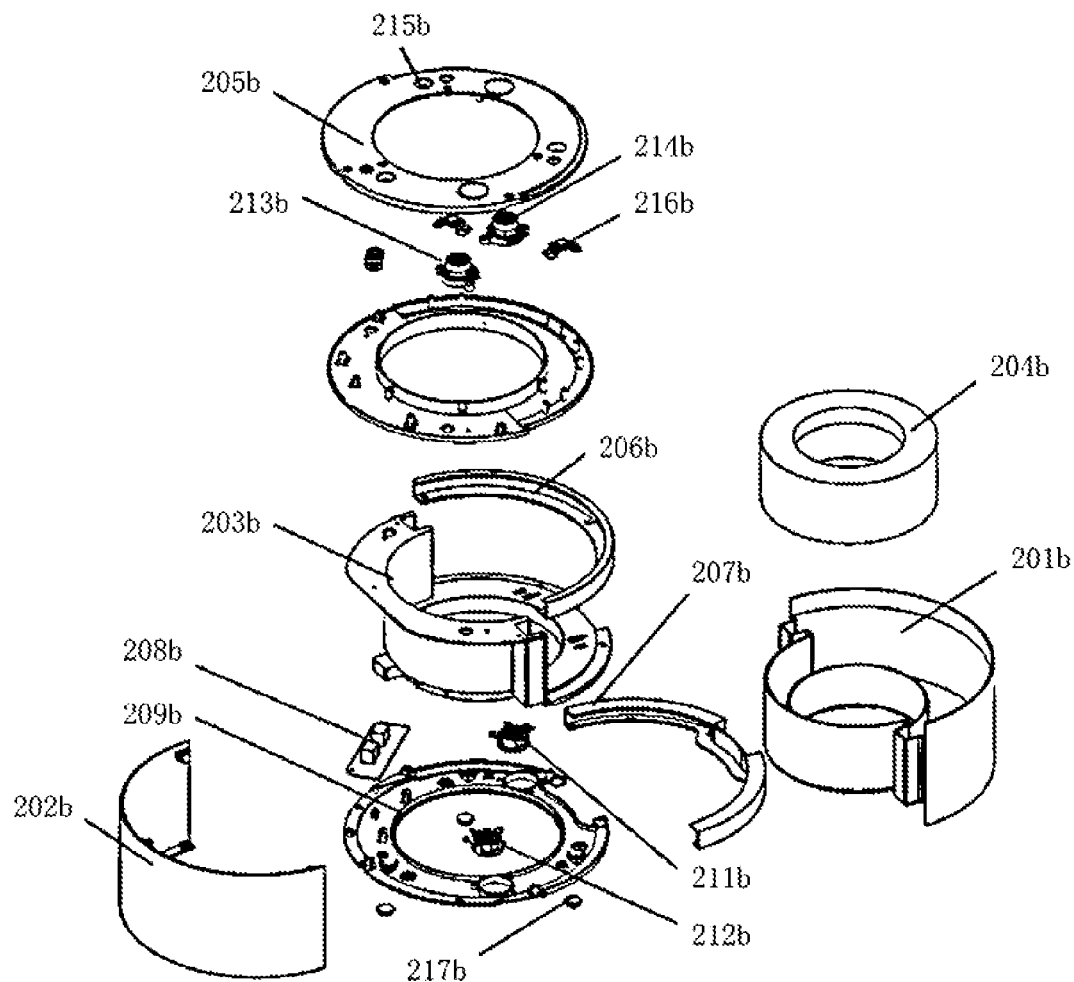
FIG. 29 is a fourth schematic view of the further humidifying device in some illustrative embodiments.

In the pure humidifying device of the prior art, a water tank special for storing water is generally provided, and then the function of evaporating humidification is realized by means of a water channel (or a water reservoir); in this embodiment, only the water tank 201b is provided, which water tank 201b is configured as shown in FIG. 28, and may be regarded as a water channel, and the water tank 201b is not only used for storing water, but also serves as a water channel. This design simplifies the structure of the prior art humidifying device and makes efficient use of the space, and the water tank 201b can be designed to be larger without considering the space occupied by the water channel.

Furthermore, since the water tank 201b surrounds the air duct, the water tank 201b has a hollow structure, allowing the wind to pass through the water tank 201b, so as to remove the water vapour around the air duct, i.e., the water vapour in the water tank 201b, which can rapidly play the role of humidification.

In some optional embodiments, an inner wall 211b of the water tank 201 surrounds the air duct, and the filter element 204b is provided with a cavity penetrating through the upper and lower surfaces of the filter element. The filter element 204b is fitted over the outer side of the inner wall 201b of the water tank via the cavity. The filter element 204b functions to improve the evaporation efficiency and purify the water in the water tank; therefore, the filter element 204b is also designed to annularly extend along the air duct to match with the annular structure in the water tank 201b so as to allow the air to pass through the water tank 201b and also to pass through the filter element 204b, thereby increasing the humidifying rate.

Further, in order to increase the area of the filter element 204b in contact with the wind, in the process of designing the cavity structure of the filter element 204b, the filter element 204b is higher than the inner wall 211b of the water tank 201b. The inner wall 211b of the water tank 201b is lower than the outer wall 212b, and the height of the filter element 204b is the same as the height of the outer wall 212b; therefore, the area of the filter element 204b in contact with the wind throughout the humidification process comprises, in addition to the area of the upper surface, the area of a side wall of the filter element 204b that is higher than the inner wall 211b.

Further, the cavity of the filter element 204b may be further modified such that the area of the bottom of the cavity is larger than the area of the top of the cavity, that is, the cavity of the filter element 204b is shaped to have a larger upper opening and a smaller lower opening to increase the area of the side surface in contact with the wind, so that the wind is in better contact with the filter element 204b and removes water vapour.

Optionally, the part of the filter element 204b that is higher than the inner wall of the water tank may be provided with a bent portion which is bent inwardly, so as to achieve the following effects: first, increasing the area of the filter element 204b in contact with the wind; second, increasing the area of the upper surface of the filter element 204b; and third, making the wind in full contact with the filter element 204b due to the reduced upper opening, so as to remove more water vapour.

Optionally, the filter element 204b may be designed to be tapered, and the structure of the inner wall of the corresponding water tank 201b may be configured accordingly.

In some illustrative embodiments, the water tank 201b is separate from the housing of the humidifying device, and the humidifying housing is provided with a groove for having the water tank placed therein.

The housing of the humidifying device comprises a humidifying top cover 205b, a humidifying housing 202b, an inner humidifying housing 203b and a humidifying chassis 209b. The inner humidifying housing 203b is fixedly connected to the humidifying housing 204b in such a manner as to be screw-connected, adhesive bonded or snap-fitted etc., the inner humidifying housing 203b is provided with a groove the structure of which matches with the water tank 201b, so that the water tank 201b can be freely detached from the housing of the humidifying device for the convenience of the user. The upper portion of the water tank 201b is then connected to the inner humidifying housing 203b via an upper connecting bar 206b, and the lower portions of the inner humidifying housing 203b and the humidifying housing 202b are fixedly connected to the humidifying chassis 209b in such a manner as to be screw-connected, adhesive bonded or snap-fitted etc.

Furthermore, the bottom of the inner humidifying housing 203b is spaced from the humidifying chassis 209b by a certain distance, and a humidifying computer board (i.e. a humidifying PCB) for controlling the humidifying device is provided in the gap between the humidifying casing 202b and the inner humidifying housing 203b; the side of the inner humidifying housing 203b that is surrounded by the humidifying housing 202b may be fixed to the humidifying chassis 209b via a bolt and the bottom edge of the other side of the inner humidifying housing 203b may be connected to the humidification chassis 209b via the lower connecting bar 207b.

Optionally, a slide rail may be provided on the groove of the inner humidifying housing 203b and a slideway may be provided in the corresponding position on the bottom of the water tank 202b to facilitate the removal of the water tank 202b more quickly and effortlessly.

Optionally, the humidifying top cover 205 is provided with an air outlet, the upper surface of the filter element 204 in the water tank 201 can be observed from the air outlet, that is, it is understood that the upper surface of the filter element 204 is exposed to the air, so that the diameter of the air outlet is prevented from being designed too small, hindering the evaporation and escaping rates of the water vapour.

Optionally, the humidifying top cover 205b is not disposed directly on the upper surface which is formed by the inner humidifying housing 203b and the upper connecting bar 206b, and the humidifying top cover 205b is spaced from the upper surface at a distance in which a series of assemblies are provided, such as a power source interface and a communication interface. A lower power source interface 213b and a lower communication interface 214b are provided on the humidifying top cover 205b; and similarly, a corresponding upper power source interface 211b and upper communication interface 212b are also provided on the humidifying chassis. Therefore, it is necessary to provide an insulating cover 210b for insulating the water vapour between the humidifying top cover 205b and the upper surface which is formed by the inner humidifying housing 203b and the upper connecting bar 206b, and the humidifying top cover 205b is fixedly connected to the insulating cover 210b. The lower power source interface 213b, the lower communication interface 214b, the upper power source interface 211b and the upper communication interface 212b may employ the structure of the first terminal block or the second terminal block of the connector as described above.

In some optional embodiments, the air duct runs through the centre of the humidifying device and is also located in the centre of the filter element 204b.

Since the air duct needs to pass through the whole humidifying device, the whole humidifying device can be regarded as a ring-like structure (in cross section), the shapes of the inner and outer rings may be the same or different, and the inner or outer ring may be of a round, square or triangular structure; and the humidifying device is preferably concentrically ring-shaped, i.e. the structure as shown in FIGS. 17-20, and this design is more conducive to ventilation and evaporation of the water vapour.

Optionally, the shape of the inner ring defines the structure of the air duct, and the longitudinal section of the air duct may be rectangular or be of other structures such as a trapezoid; for a better understanding, if the longitudinal section of the air duct is rectangular, it is approximately understood that the air duct is of a cylinder or cubic structure, and if the longitudinal section is a trapezoidal, the air duct may be of a nearly circular cone structure.

Optionally, the humidifying device is provided with a connecting structure which is connected to the other devices as described above; the connecting structure may be a guiding structure, such as a guide groove and a guide post, the guide post and the corresponding guide groove of the respective devices being arranged to mate with each other, for example, a guide groove 215b is provided on the humidifying top cover 205b, and a guide post is provided on the humidifying chassis. In addition, a lower magnet 216b and an upper magnet 217b may be also respectively provided on the humidifying top cover 205b and the humidifying chassis 209b, so that the humidifying device is connected to other devices by means of attraction.

With the above embodiment, the following effects can be achieved: a simple structure, a good safety performance, no "white-powder" pollution, and easy to clean the device; and the principle of natural evaporation is adopted, such that the present invention is more green and healthy.

The various embodiments of the present specification are described in a progressive manner, each of the embodiments is explained with priority given to the points different from those of the other embodiments, and the same and similar parts of the various embodiments can be referred to each other. The foregoing description of the disclosed embodiments will enable those skilled in the art to implement or use the present invention. Numerous modifications to these embodiments will be readily apparent to those skilled in the art, and the generic principles defined herein may be implemented in other embodiments without departing from the spirit or scope of the present invention. Accordingly, the present invention is not to be limited to the embodiments shown herein, but is to be accorded the widest scope consistent with the principles and novel features disclosed herein.

What is claimed is:

1. An air handling system, characterized by comprising a top cover, a base and at least one air handling device provided between the top cover and the base,
    wherein the top cover and the adjacent air handling device, the base and the adjacent air handling device, and the adjacent air handling devices are all connected to each other by means of magnetic attraction,
    wherein at least one guide groove is provided on the bottom surface of the top cover and the bottom surface of the air handling device, respectively; at least one guide protrusion is provided on the top surface of the base and the top surface of the air handling device, respectively; and the guide groove and the guide protrusion which are provided on the adjacent two surfaces positionally correspond to each other such that the guide protrusion is inserted into the guide groove,
    wherein an electrically conductive sheet is provided in the guide groove, and the guide protrusion is an electric conductor.

2. The air handling system according to claim 1, characterized in that at least one magnetic component is provided on the bottom surface of the top cover, on the top and bottom surfaces of the air handling device, and on the top surface of the base, respectively.

3. The air handling system according to claim 2, characterized in that the magnetic component on the bottom surface of the top cover positionally corresponds to the magnetic component on the top surface of the uppermost air handling device, and the polarities of the corresponding magnetic components are opposite.

4. The air handling system according to claim 2, characterized in that the magnetic component on the top surface of the base positionally corresponds to the magnetic component on the bottom surface of the lowermost air handling device, and the polarities of the corresponding magnetic components are opposite.

5. The air handling system according to claim 2, characterized in that the magnetic component on the top surface of the air handling device corresponds to the magnetic component on the bottom surface of the adjacent air handling device, and the polarities of the corresponding magnetic components are opposite.

6. The air handling system according to claim 2, characterized in that the magnetic components are provided on the bottom surface of the top cover, on the top and bottom surfaces of the air handling device, or in the centre or on the circumference of the top surface of the base.

7. The air handling system according to claim 1, characterized in that the at least one air handling device comprises at least one of a humidifying device, a dehumidifying device and a purifier.

* * * * *